United States Patent [19]

Peterson et al.

[11] 4,200,110
[45] Apr. 29, 1980

[54] FIBER OPTIC PH PROBE

[75] Inventors: John I. Peterson, Falls Church, Va.; Seth R. Goldstein, Bethesda, Md.

[73] Assignee: United States of America, Washington, D.C.

[21] Appl. No.: 855,384

[22] Filed: Nov. 28, 1977

[51] Int. Cl.$^2$ .................... A61B 5/00; G01N 21/00
[52] U.S. Cl. .................... 128/634; 128/636; 356/39; 356/412; 422/58; 23/230 B
[58] Field of Search .......... 128/2 G, 2 L, 2 E, 2.1 E, 128/633, 634, 636; 356/39, 42, 182, 243, 412; 252/408; 422/58

[56] References Cited

U.S. PATENT DOCUMENTS

| 2,084,399 | 6/1937 | Kuettel | 260/42.21 |
|---|---|---|---|
| 3,164,663 | 1/1965 | Gale | 250/574 |
| 3,183,208 | 5/1965 | Jurgeleit | 260/42.21 |
| 3,787,119 | 1/1974 | Rybak | 356/39 |
| 3,814,081 | 6/1974 | Mori | 128/2 L |
| 4,016,133 | 4/1977 | Hyosu et al. | 260/42.21 |
| 4,016,863 | 4/1977 | Brantigan | 128/2 G |
| 4,033,330 | 7/1977 | Willis et al. | 128/2 G |
| 4,041,932 | 8/1977 | Fostick | 128/2 G |

FOREIGN PATENT DOCUMENTS 770889 3/1957 United Kingdom .

OTHER PUBLICATIONS

Dardik, Herbert; *On-Line in Vivo Measurements of Partial Pressures of Oxygen and Carbon Dioxide of Blood, Tissue, and Respired Air by Mass Spectrometry*, in Surg., Gyn. & Obs., Dec. 1970, pp. 1157–1160.

*Primary Examiner*—Robert W. Michell
*Assistant Examiner*—Arthur S. Rose
*Attorney, Agent, or Firm*—Holman & Stern

[57] ABSTRACT

A fiber optic pH probe suitable to be implanted in tissue for physiological studies is disclosed. The probe includes an ion permeable membrane envelope which encloses the ends of a pair of optical fibers. A pH sensitive dye indicator composition is present within the envelope. The probe operates on the concept of optically detecting the change in color of a pH sensitive dye.

8 Claims, 3 Drawing Figures

FIBER OPTIC PH PROBE

BACKGROUND AND SUMMARY OF THE INVENTION

The present invention relates to a fiber optic pH probe which is suitable to be implanted in the body of a human or other animal for physiological studies. More particularly, the present invention relates to a fiber optic pH probe in the form of a miniature pH sensor, constructed with the use of reversible dye indicators and single fiber optics, which is small enough to pass through a 22 gauge hypodermic needle and which can be implanted in tissue for physiological studies. The device is particularly well suited for use during exercise of the subject being studied.

A determination of pH is desirable in a wide variety of biological studies. In particular, for studies of blood oxygen content, pH is an important parameter for the oxygen-hemoglobin dissociation curve. For some diseases, e.g., sickle cell anemia, it is desirable to determine this curve in vivo during exercise.

Previous pH sensors have included sensors such as the glass electrode pH sensor built into a hypodermic needle as described by J. D. Czaban et al., *Analytical Chemistry*, 47, No. 11, 1787-92 (September 1975) and ibid., 48, No. 2, 277-81 (February 1976). While such electrodes are suitable for some purposes, their rigid needle construction is not desirable in certain physiological studies, such as exercise studies, because of irritation. Furthermore, such electrode systems have the inherent risk of electrical hazard.

Other devices for measuring pH are described, for example, in U.S. Pat. Nos. 4,033,330 and 4,041,932. Such prior art devices are designed to measure pH from outside the body and are not constructed so as to be easily implanted within the body.

By the present invention, there is provided an implantable pH measuring device which is of flexible construction and which can be placed in muscle or other tissue for in vitro or in vivo use without a needle remaining. The pH probe of the present invention is easily assembled, is potentially very low in cost and is thus capable of being readily manufactured in quantity for use as a disposable item. The present pH probe includes an ion permeable membrane envelope which encloses the ends of a pair of optical fibers. A pH sensitive dye indicator composition is present within the envelope. The probe operates on the concept of optically detecting the change in color of a pH sensitive dye.

BRIEF DESCRIPTION OF THE DRAWINGS

The advantages and features of the present invention will be more fully understood from the following description of the preferred embodiments, taken in conjunction with the accompanying drawings, wherein.

DESCRIPTION OF THE PREFERRED EMBODIMENTS

Figure 1:
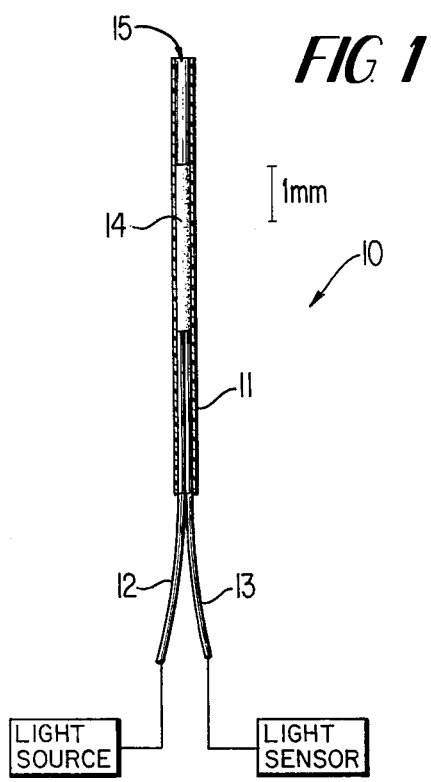
FIG. 1 is a perspective view of the distal end of the pH probe of the present invention.

In the embodiment of the invention as illustrated in FIG. 1, there is shown a fiber optic pH probe 10 which includes an ion permeable membrane envelope 11 which encloses the distal ends of a pair of optical fibers 12, 13. The envelope 11 is preferably in tubular form, i.e., a hollow, elongated cylinder, which fits closely about the two fibers 12, 13. Retained within the membrane 11 and distal to the ends of the fibers 12, 13 is a pH-indicating dye-containing composition 14. A suitable sealing material such as, for example, ultraviolet light-setting optical cement, is employed to seal the distal end 15 of the membrane 11. Such sealing material is also employed where the optical fibers 12, 13 enter the membrane 11, in order to hold the assembly securely together.

The membrane envelope 11 may be of any suitable material which is sturdy enough to provide a protective sheath for the components enclosed therein while being sufficiently flexible or non-brittle so as to be readily positioned within various parts of the body without breaking. An additional requirement for the membrane 11 is that it have pores of a size large enough to allow passage of hydrogen ions while being sufficiently small so as to preclude passage of the dye materials. One membrane 11 material which has been employed with good results is a dialysis tubing known as Cuprophane B4AH, a regenerated cellulose material having the properties as shown in Table I.

TABLE I

| Measured Membrane Strength Properties of Cuprophane B4 AH | |
| --- | --- |
| Ultimate Tensile Strength | Ultimate Break Elongation |
| Greater than 300 Grams | Greater than 20% |

This particular Cuprophane tubing which was employed had an inner diameter of 300 microns and a wall thickness of 19 microns.

The pH-indicating dye-containing material 14 may be any of various such materials which, when employed in conjunction with the membrane 11, will result in the dye being retained in the optical region within the membrane 11 without diffusing therethrough, and which will provide an indication of pH within the range of interest.

In selecting the dye material 14, it should be kept in mind that the material 14 to be employed may be a dye itself, if the dye molecules of the particular dye are sufficiently large that the dye will not diffuse out of the optical region through the walls of the membrane 11. Examples of such dyes are the "natural" dyes obtained from plants, such as azolitmin. Such dyes are of such molecular size that they will not diffuse readily and can be used as pH indicators. If the dye itself is employed rather than a larger molecular weight composition such as a polymer to which the dye is attached, one problem which may arise is that the corresponding membrane 11 employed with such relatively low molecular weight dye materials will have a pore size which will be so small as to result in a rate of diffusion of hydrogen ions which is too slow to provide a good speed of response to pH. This is particularly true when it is desired to measure rapid changes of pH during exercise of the patient being studied.

If the dye to be employed does not have sufficient molecular size, an alternative procedure is to employ a dye which is bound to another material, such as a polymer. The dyes which are usually employed include pH indicating dyes such as phthaleins, and sulfonphthaleins.

Methods for bonding such dyes with other molecules include such known procedures as the use of a Mannich - type reaction, i.e., formaldehyde condensation of the dye with an amine group, as in preparation of the complexones. Such reactions are described, for example, in the following publications, incorporated herein by reference: R. O. Cinneide, *Nature,* 175, 47 (Jan. 1, 1955); R. Prible, *Analyst,* 83, 188–95 (1958); Swiss Pat. No. 298, 194 (July 1, 1954); U.S. Pat. No. 2,745,720; and G. Schwartzenbach et al., *Complexometric Titrations,* Methuen Press (Barnes and Noble), 1969. Another approach which attaches the dye to a polymer is to derivatize the polymer, i.e., attach groups such as an amino group to the polymer so that the dye can be subsequently reacted, such methods being described for example, by J. K. Inman et al., *Biochemistry,* 8, 4074–82 (1969), incorporated herein by reference. These techniques require prior formation of a polymer, with subsequent dye attachment.

Another method of attaching a pH indicating dye to another material is that which employs dyes with the isothiocyanate group attached, such dyes being synthesized by a process as described, for example, in U.S. Pat. No. 2,937,186, incorporated herein by reference. Examples of such dyes include 5(6) Rhodamine B - CNS and Fluorescein - CNS, both of which are available from Eastman Organic Chemical Co. A dye with the - CNS group on it reacts, via this group with active hydrogens and therefore can be attached to many other types of moieties, as described, for example, in U.S. Pat. No. 3,847,745 and also in J. J. Haaijman et al., *Journal of Immunological Methods,* 5, 359–74 (1974), both of which are incorporated by reference. The latter publication describes the attachment of fluorescein and rhodamine isothiocyanates to Sephadex beads, a polysaccharide hydrophilic polymer available from the Pharmacia Corp.

A chemical method of attaching dyes in general involves the use of cyanuric chloride which will react with an amino group on a dye, and this will then react with an amino or hydroxyl group on a support to chemically link the dye to the support. Such methods are described, for example, in C. V. Stead, *The Chemistry of Reactive Dyes and Its Relevance to Intracellular Staining Techniques,* pp 41–59; and also in S. B. Katen et al., *Intracellular Staining in Neurobiology,* Springer - Verlag (1973), both of which are incorporated by reference.

Dyes for pH indication may also be prepared by microencapsulation, employing techniques as described, for example, in *Science,* 193, 134–137 (July 9, 1976), incorporated herein by reference. Another method for preparing dye compositions is that in which free radical polymerizable gels, e.g., acrylates, are prepared, containing a functional group on the monomer, such as hydroxyl, amine or amide, with the dye being reacted with the functional group either before or after polymerization.

A method for bonding the dye to a hydrophilic polymer is still another alternative procedure which may be employed to produce a dye-containing material suitable for use in the pH probe of the present invention. In this procedure, a suitable dye is copolymerized with an acrylic based monomer such as acrylamide, methyl methacrylate or hydroxymethyl methacrylate (Hydron) to form a hydrophilic copolymer in which the pH indicating dye is bound so that a non-diffusible form of the dye is produced. Specific dyes which may be copolymerized in this manner include phenol red, brilliant yellow (CI24890) and rosolic acid. In addition the dye - polymer combination can be produced in the form of microbeads by emulsion (water-in oil) polymerization. Specific methods for preparation of such copolymers in described in the U.S. patent application Ser. No. 855,397 filed simultaneously herewith, in the name of John I. Peterson, said application being commonly assigned, which application is incorporated herein by reference.

The following examples are illustrative methods of the present invention.

EXAMPLE 1

Method of making dye polyacrylamide microspheres

Dissolve 10 mg of phenol red in 2.0 ml of 6M acrylamide (containing 0.06 M N,N-methylene bisacrylamide). Dissolve about 50 mg ammonium persulfate in this solution, add 0.5 g Span 80; Tween 80-85: 15 parts by weight emulsifier mixture. Then add 10 ml of toluene and shake well in a test tube. Bubble nitrogen through the solution for 5 minutes, add 4 drops of tetramethylethylenediamine (TMED), shake well, continue slow bubbling of nitrogen for 15 minutes. The heat of reaction should be evident after about 1 minute following addition of TMED. Wash the resulting microspheres in a centrifuge as follows: (1) three times with ethanol: water (1:1 ratio), with sodium hydroxide solution added as needed to make the dye basic (purple color); (2) once with acetic acid solution added to make the dye acidic (red color); (3) twice with ethanol; and filter by suction until dry.

EXAMPLE 2

Addition of light scattering microspheres of polystyrene

A polystyrene microsphere latex (water suspension), such as Dow Diagnostics uniform latex particles of 0.945 micron diameter, is freeze-dried (lyophilized) to convert it to a dry powder without agglomeration of the particles. This powder is then mechanically mixed with the dried dyed polyacrylamide microspheres as prepared in Example 1. A mixture of 12 mg of polystyrene microspheres to 10 mg of the polyacrylamide microspheres of Example 1 was determined to be optimum. In the use of this mixture, the mixture may be packed tightly, in dry form, into the hollow membrane of the pH probe previously discussed, which has been assembled onto the optical fibers, and the assembly sealed with UV curing optical cement.

The optical fibers 12, 13 may be of a length such as about 6 feet, for example, so as to provide adequate flexibility of movement of the device 10 relative to a light source and a light sensor, both of which may be of conventional construction and thus are shown in the drawings as boxes. One of the fibers 12 is connected at its proximal end to the light source while the other fiber 13 is connected at its proximal end to the light sensor. The fibers 12, 13 are of conventional construction, with one of the fibers employed to conduct light toward the probe 10 from the light source, while the other fiber is employed to receive and conduct light from the probe 10 to the sensor. The fibers 12, 13 may be, for example, plastic optic fibers having a diameter of about ⅛ mm. The two fibers 12, 13 may be enclosed along their length exterior to the probe by a 1 mm diameter Teflon tubing for mechanical protection.

The indicator dye, phenol red, is an organic acid (HA) which dissociates into hydrogen ion (H+), and an anion, (A−) according to the following equilibrium:

$$K = \frac{(H+)(A-)}{(HA)} = \text{constant}$$

where the brackets represent solution activities or concentrations. By definition, pH=log [1/(H+)], so that $$pH = -\log K + \log \frac{(A-)}{(HA)} = pK - \log\left(\frac{\text{constant}}{\text{optical density of A}-} - 1\right)$$

Figure 2:
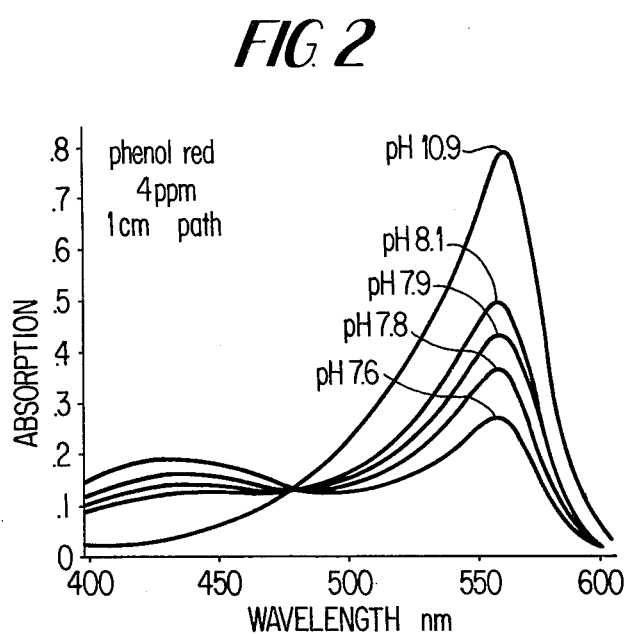
FIG. 2 is a graph showing indicator dye optical absorption.

The (A−) absorbs light at 560 nm as a function of its concentration as shown experimentally in FIG. 2, and the (HA) is not independent of (A−). Thus pH and optical density at 560 nm are uniquely related. Since the absorbance of 485 nm is not a function of pH, (see FIG. 2), this wavelength can be used as a reference for normalizing the 560 nm light. An alternative is to use light at a wavelength greater than 600 nm which is also independent of pH since the dye does not absorb light in that region of the spectrum. In the probe 10, where the light is backscattered through the dye from one fiber into the other fiber, it happens that over the pH range of interest, the relation between pH and the ratio of intensity at 560 nm to the intensity at 485 nm is linear, as shown in the data of FIG. 3.

As previously mentioned, the light source and light sensor are of conventional construction. Thus, for example, excitation light may be provided by a 150 watt tungsten high intensity projection lamp (ELV). Forced convection cooling, and an infrared reflecting "heat mirror" are used to prevent the plastic fiber from overheating. The large numerical aperture of the plastic fiber (approximately 1.2 radians total included angle) aids in efficient light collection. Measurement of the return light may be performed by a solid state photodiode operational amplifier combination (such as EG&G HAV-4000A) followed by a high gain istrumentation amplifier. Eight narrow band interference filters (approximately 5 nm wide half power points) with central wavelengths at 560 and 485 nm are alternated on a motor driven wheel placed between the exit of the return fiber and the light sensor. An alternative is to use a single filter for 560 nm light and a single filter for 485 nm light (or red light) which are alternately positioned in place by a stepper motor. The increased dwell time allows more time for electronic signal averaging and subsequent noise suppression. Synchronization pulses generated by two additional photodiodes detecting light shining through appropriately placed holes in the filter wheel control three sample-and-hold modules which measure the sensor output for (a) 560 nm light, (b) 485 (or red) nm light, and (c) no input light. The temperature sensitive "dark" output is subtracted from the other two outputs, along with the output due to ambient light (when the excitation light is off) before the light signal ratio is taken in an analog divider. Gain and level adjustments are subsequently made so that pH is directly displayed on a digital voltmeter.

In preparing the dye-containing material 14, light scattering particles such as, for example, polystyrene microspheres, of about 1 micron diameter, may be added prior to incorporation of the dye material 14 into the hollow membrane 11.

Figure 3:
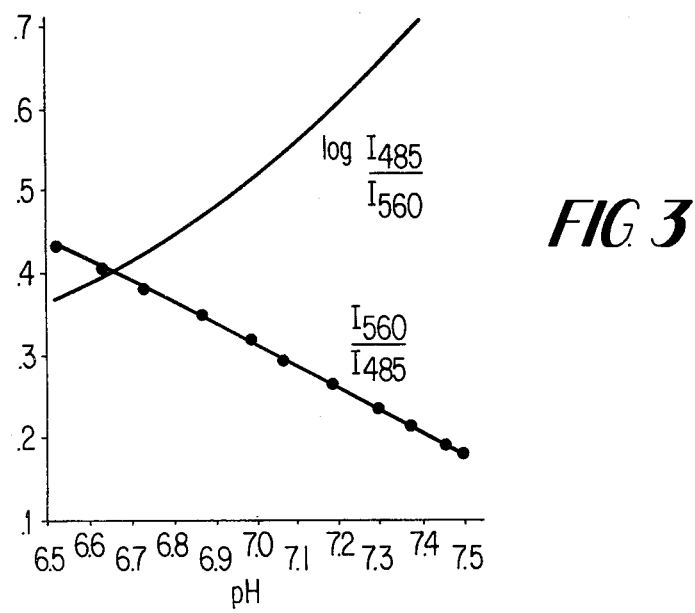
FIG. 3 is a graph showing an experimental determination of returned light intensity ratio as a function of pH.

The in vitro test measurements with the basic probe shown in FIG. 3 were performed with a laboratory spectrometer and have a standard deviation of 0.01 pH units. The probe dynamic response can be roughly characterized by a 0.7 minute time constant, its temperature coefficient is 0.02 pH units/° C., and the ionic strength coefficient at 37° C. is 0.01 pH units/8% change in ionic strength.

It is thought that the invention and many of its attendant advantages will be understood from the foregoing description and it will be apparent that various changes may be made in the form, construction and arrangement of the parts without departing from the spirit and scope of the invention or sacrificing its material advantages, the forms hereinbefore described being merely preferred embodiments thereof.

The embodiments of the invention in which an exclusive property or privilege is claimed are defined as follows:

1. A fiber optic pH probe suitable to be implanted in tissue for physiological studies, comprising: an ion permeable membrane in the form of a hollow, elongated cylinder having a distal end and a proximal end, said membrane being sealed at the distal end thereof; a pair of optical fibers having distal and proximal ends located substantially parallel to each other and adjacent to each other at their distal ends, said fiber distal ends being located within the proximal end of said hollow membrane; pH sensitive color-changing dye-containing solid material located within said hollow membrane, said ion permeable membrane having pores of a size large enough to allow passage of hydrogen ions while being sufficiently small so as to preclude passage of the dye-containing material.

2. The probe of claim 1, further including a light source connected to the proximal end of one of said optical fibers and light sensor means connected to the proximal end of the other optical fiber.

3. The probe of claim 1, wherein said dye-containing solid material comprises a hydrophilic copolymer of an acrylic based monomer and a dye.

4. The probe of claim 3, wherein said acrylic based monomer is selected from the group consisting of acrylamide, methyl methacrylate and hydroxymethyl methacrylate.

5. The probe of claim 3, wherein said dye is selected from the group consisting of phenol red, rosolic acid, or brillant yellow (CI 24890).

6. The probe of claim 1, wherein said dye-containing solid material is present in the form of microbeads.

7. The probe of claim 1, wherein light scattering particles are incorporated with said dye-containing material.

8. The probe of claim 7, wherein said light scattering particles comprise polystyrene microspheres.

* * * * *